United States Patent [19]
Lademann et al.

[11] 3,962,336
[45] June 8, 1976

[54] PROCESS FOR THE PREPARATION OF 5-CHLORO-2-TOLUIDINE

[75] Inventors: Rudolf Lademann, Kelkheim, Taunus; Franz Landauer, Frankfurt am Main, both of Germany

[73] Assignee: Hoechst Aktiengesellschaft, Frankfurt am Main, Germany

[22] Filed: Apr. 16, 1974

[21] Appl. No.: 461,453

[30] Foreign Application Priority Data

Apr. 18, 1973 Germany.............................. 2319645

[52] U.S. Cl. ............................................. 260/579
[51] Int. Cl.² ........................................ C07C 85/24
[58] Field of Search .................................... 260/579

[56] References Cited

UNITED STATES PATENTS

| | | | |
|---|---|---|---|
| 1,930,751 | 10/1933 | Havas et al. | 260/579 X |
| 1,930,752 | 10/1933 | Havas et al. | 260/579 X |
| 2,675,409 | 4/1954 | Orloff et al. | 260/579 |

*Primary Examiner*—Paul Shaver
*Attorney, Agent, or Firm*—Curtis, Morris & Safford

[57] ABSTRACT

The hydrochloride of 5-chloro-2-toluidine is obtained by dispersing 2-toluidine hydrochloride in a halohydrocarbon and reacting it with chlorine. No isomers are formed and very little higher chlorinated products. 5-chloro-2-toluidine is easily set free from the hydrochloride with aqueous bases.

8 Claims, No Drawings

PROCESS FOR THE PREPARATION OF 5-CHLORO-2-TOLUIDINE

This invention relates to a process for the preparation of 5-chloro-2-toluidine.

It is known that hydrohalides of aniline can be reacted with halogens, such as chlorine (cf. U.S. Patent No. 2,675,409). For example, when aniline-hydrochloride is chlorinated in carbon tetrachloride, 2.4.6-trichloroaniline-hydrochloride is obtained.

When 2-toluidine is chlorinated, the keto-chloride $C_7H_5Cl_5O$ (cf. Zinke, Ann. 394, 3) is obtained. Therefore, processes for the nuclear chlorination of the 2-toluidine so far have been based on N-acyl compounds, for example, the N-acetyltoluidide. However, these processes have the disadvantage that the N-acyl compound must primarily be prepared and the acyl group must again be split off after the chlorination. For processes on an industrial scale this procedure constitutes a great drawback because additional energy and time-consuming operational steps are necessary. Moreover, such a process has the disadvantage that highly diluted aqueous solutions are obtained in addition to chlorotoluidine upon the saponification of the acyl group. The acids formed, or mostly the alkali metal salts thereof formed because of alkaline splitting, cannot be regenerated therefrom any longer by economical methods. Therefore, they are often deposited into the waste water as dilute aqueous solutions, for example, as sodium acetate solution which increase the biological or chemical demand for oxygen.

Now, surprisingly, a simpler process was found for the preparation of 5-chloro-2-toluidine hydrochloride or the free amine, respectively, which comprises reacting 2-toluidine hydrochloride as a suspension in a halogenated hydrocarbon at a temperature ranging from about 10° to about 70°C, preferably about 20° to about 45°C with the amount of chlorine calculated for monochloro-toluidine and, optionally, setting free the amine from the 5-chloro-2-toluidine-hydrochloride with a base.

The process of the invention has the advantage that, starting from 2-toluidine, the protection of the amino group apparently necessary for the chlorination is reached in the shortest time by the rapid salt formation with hydrogen chloride and the hydrogen chloride necessarily formed in the chlorination can be reused for the formation of hydrochloride, which is significant. This recycling allows the waste water to remain free from organic contaminations, for example, sodium acetate or sodium formate as it is the case with known processes.

A further advantage of the process of the invention is that the technical expenditure can be reduced, for the acylamino compounds formerly used in the chlorination had to be prepared from toluidine by heating for a long time with an organic acid and distilling off the water formed. These operations required particular apparatuses and a considerable expenditure of energy. Contrary thereto, the hydrochloride is formed in less than a tenth of the time and without additional apparatuses, because there is no water formed in the salt formation causing serious troubles to the reaction and thus the reaction vessel for the chlorination can also be used for the salt formation. As the formation of the hydrochloride takes place without heat supply there is no consumption of energy.

The same advantages are given in the isolation of the pure chlorotoluidine after the chlorination, unless the hydrochloride formed is used for further working without conversion into the free amine. According to the usual preparation methods, the acyl group had to be split off by a mostly alkaline treatment by heating over a longer period, that is to say, by supplying energy, whereas according to the invention the amine is directly set free in an ion reaction by adding bases, such as alkali metal hydroxide at room temperature or at slightly elevated temperature.

After distilling off the solvent or suspension agent necessary in both cases, the crude 5-chloro-2-toluidine can be purified by fractionated distillation.

According to the invention the inert solvents or suspension agents used are halogenated hydrocarbons, preferably, chlorohydrocarbons or fluorochlorohydrocarbons. As chlorohydrocarbons, there may be mentioned, for example, chloroform, carbon tetrachloride, tetrachloroethane, dichlorobenzenes, such as o-dichlorobenzene and, preferably, chlorobenzene. Of course, mixtures of these chlorohydrocarbons may also be used, optionally in mixture with other halohydrocarbons.

The reaction may be carried out in suitable apparatuses, continuously or discontinuously, pressureless or under elevated pressure. Generally, the process of the invention is carried out in such a manner that the 2-toluidine dissolved in the inert chlorohydrocarbon is treated with approximately molar amounts of gaseous hydrogen chloride. The suspension of the hydrochloride formed is then chlorinated, the chlorine being led to the surface of the well stirred suspension, preferably, however, directly into the suspension.

To avoid a greater portion of products having a higher chlorine content not more than about 1.2 mol of chlorine, preferably about 0.8 to about 1 mol of chlorine are advantageously used. Of course, less than 0.8 mol of chlorine can also be used, whereupon only the amount of non chlorinated toluidine to be recycled is greater.

The reaction temperature is within the range of from about 10°C to about 70°C, preferably from 20°C to 45°C.

After chlorination, the suspended 5-chloro-2-toluidine is freed from the hydrogen chloride still dissolved by blowing with air or nitrogen. The hydrogen chloride can be reused for further hydrochloride formation practically without purification together with the hydrogen chloride which had already evolved in the chlorination.

If there is no intention to reuse the hydrogen chloride, blowing out is not necessary and the suspension can directly be treated with bases, for example, sodium hydroxide solution, the amount of base being correspondigly higher in this case. After separation of the salt solution obtained, for example, a sodium chloride solution, the solvent is primarily distilled from the organic phase. For further purification, the remaining 5-chloro-2-toluidine can be subjected to fractionated distillation.

However, the 5-chloro-2-toluidine can also be isolated by removing the solvent by means of steam after the chlorination, and, optionally, after the blowing operation and by isolating the free amine from the aqueous solution of the hydrochloride by adding a base, preferably aqueous or solid alkali metal hydroxide.

It is especially surprising that practically no other isomers, for example the 3-chloro-2-toluidine, are formed in the process of the invention, which simplifies the working up of the 5-chloro-2-toluidine by distillation.

The 5-chloro-2-toluidine is a valuable intermediate for dyestuffs and insecticides.

The following example illustrates the invention.

EXAMPLE:

57 g of hydrogen chloride (= 1.56 mols) were introduced, while thoroughly stirring, into a solution of 160 g of distilled o-toluidine (= 1.5 mols) in 1300 ml of chlorobenzene in the course of 30 – 45 minutes. It is advisable but not necessary to cool the reaction mixture slightly in a water bath. 105 g of chlorine gas (= 1.48 mols) were introduced at 35°C within 1¾ hours. Then, the hydrogen chloride still in solution was blown out with air. The hydrochloride was suction-filtered through a Buchner funnel and dried in the air. To isolate the free 5-chloro-2-toluidine the dried filter residue was introduced portionwise into 350 g of sodium hydroxide solution (18%). The temperature rose to about 40° – about 50°C. Then, the crude amine was separated in a separating funnel and subjected to a fractionated distillation under reduced pressure. The amount of product obtained was 60.1 g of 2-toluidine (= 0.56 mol), which was reused, 101.0 g of 5-chloro-2-toluidine (= 0.71 mol) corresponding to 75.5 % calculated on reacted 2-toluidine (introduced 2-toluidine minus 2-toluidine recovered) and 14.3 g of 3.5-dichlorotoluidine (= 0.08 mol).

We claim:

1. A process for the preparation of the hydrochloride of 5-chloro-2-toluidine which comprises reacting a suspension of 2-toluidine hydrochloride in an inert halohydrocarbon solvent with less than the 1.2-fold molar amount of chlorine at a temperature of 10 to 70°C.

2. A process as claimed in claim 1, wherein the temperature is 20° to 45°C.

3. A process as claimed in claim 1, wherein the halohydrocarbon is a chloro- or fluorochloro alkane of 1 or 2 carbon atoms, chlorobenzene, dichlorobenzene or a mixture of two or more of said compounds.

4. A process as claimed in claim 1, wherein the halohydrocarbon is chloroform, tetrachloromethane, tetrachloroethane, chlorobenzene or dichlorobenzene or a mixture thereof.

5. A process as claimed in claim 1, wherein the halohydrocarbon is chlorobenzene.

6. A process as claimed in claim 1, wherein 0.8 to 1 mol of chlorine are reacted per mol of 2-toluidine hydrochloride.

7. A process for the preparation of 5-chloro-2-toluidine hydrochloride which comprises reacting 2-toluidine hydrochloride with less than 1.2 molar amount of chlorine at a temperature of 10° to 70°C, said reaction being carried out in an inert halohydrocarbon solvent which is a member selected from the group consisting of chlorohydrocarbon solvent and chlorofluorohydrocarbon solvent.

8. A process of the preparation of 5-chloro-2-toluidine hydrochloride which comprises reacting 2-toluidine hydrochloride with 0.8 to 1 mole of chlorine per mole of 2-toluidine hydrochloride, at a temperature of 20° to 45°C in an inert halohydrocarbon solvent which is a member selected from the group consisting of chloroform, tetrachloromethane, tetrachloro-ethane, chlorobenzene, dichlorobenzene and mixtures thereof.

* * * * *